US009329675B2

(12) United States Patent
Öjelund et al.

(10) Patent No.: US 9,329,675 B2
(45) Date of Patent: May 3, 2016

(54) SYSTEM WITH 3D USER INTERFACE INTEGRATION

(75) Inventors: Henrik Öjelund, Lyngby (DK); David Fischer, Stenløse (DK); Karl-Josef Hollenbeck, København Ø (DK)

(73) Assignee: 3SHAPE A/S, Copenhagen K (DK)

( * ) Notice: Subject to any disclaimer, the term of this patent is extended or adjusted under 35 U.S.C. 154(b) by 249 days.

(21) Appl. No.: 13/991,513

(22) PCT Filed: Dec. 5, 2011

(86) PCT No.: PCT/DK2011/050461
§ 371 (c)(1),
(2), (4) Date: Jun. 4, 2013

(87) PCT Pub. No.: WO2012/076013
PCT Pub. Date: Jun. 14, 2012

(65) Prior Publication Data
US 2013/0257718 A1    Oct. 3, 2013

Related U.S. Application Data

(60) Provisional application No. 61/420,138, filed on Dec. 6, 2010.

(30) Foreign Application Priority Data

Dec. 6, 2010    (DK) ................................ 2010 01104

(51) Int. Cl.
*G06F 3/01*     (2006.01)
*A61C 9/00*     (2006.01)
*G01B 11/24*    (2006.01)

(52) U.S. Cl.
CPC . *G06F 3/01* (2013.01); *A61C 9/004* (2013.01); *G01B 11/24* (2013.01)

(58) Field of Classification Search
CPC combination set(s) only.
See application file for complete search history.

(56) References Cited

U.S. PATENT DOCUMENTS

| 6,135,961 | A  |   | 10/2000 | Pflugrath et al. |         |
|-----------|----|---|---------|------------------|---------|
| 6,967,644 | B1 | * | 11/2005 | Kobayashi        | 345/158 |
| 7,141,020 | B2 |   | 11/2006 | Poland et al.    |         |
| 7,813,591 | B2 | * | 10/2010 | Paley et al.     | 382/285 |
| 7,831,292 | B2 | * | 11/2010 | Quaid et al.     | 600/424 |
| 8,035,637 | B2 | * | 10/2011 | Kriveshko        | 345/419 |

(Continued)

FOREIGN PATENT DOCUMENTS

| CN | 101513350       | 8/2009 |
|----|-----------------|--------|
| WO | WO 2004/066615 A1 | 8/2004 |

(Continued)

OTHER PUBLICATIONS

Three-Dimensional Virtual Reality Xia et al. Jun. 2001.*

(Continued)

*Primary Examiner* — Van Chow
(74) *Attorney, Agent, or Firm* — Buchanan Ingersoll & Rooney PC

(57) ABSTRACT

Disclosed is a system comprising a handheld device and at least one display. The handheld device is adapted for performing at least one action in a physical 3D environment; wherein the at least one display is adapted for visually representing the physical 3D environment; and where the handheld device is adapted for remotely controlling the view with which the 3D environment is represented on the display.

19 Claims, 5 Drawing Sheets

(56) References Cited

U.S. PATENT DOCUMENTS

| | | | |
|---|---|---|---|
| 8,384,665 B1* | 2/2013 | Powers et al. | 345/156 |
| 2003/0158482 A1 | 8/2003 | Poland et al. | |
| 2004/0204787 A1* | 10/2004 | Kopelman et al. | 700/182 |
| 2005/0057745 A1 | 3/2005 | Bontje | |
| 2006/0025684 A1 | 2/2006 | Quistgaard et al. | |
| 2006/0092133 A1* | 5/2006 | Touma et al. | 345/158 |
| 2006/0146009 A1 | 7/2006 | Syrbe et al. | |
| 2009/0061381 A1 | 3/2009 | Durbin et al. | |
| 2009/0217207 A1 | 8/2009 | Kagermeier et al. | |

FOREIGN PATENT DOCUMENTS

| | | |
|---|---|---|
| WO | 2007084727 | 7/2007 |
| WO | 2009089126 | 7/2009 |
| WO | 2001011193 | 1/2011 |

OTHER PUBLICATIONS

International Search Report (PCT/ISA/210) issued on Feb. 22, 2012, by the Danish Patent Office as the International Searching Authority for International Application No. PCT/DK/2011/050461.

C. Graetzel et al., "A Non-Contact Mouse for Surgeon-Computer Interaction", Technology and Health Care, 12(3), 2004, pp. 1-19.

Sebastian Vogt et al., "An AR System With Intuitive User Interface for Manipulation and Visualization of 3D Medical Data", Stud. Health Technol. Inform., Medicine Meets Virtual Reality 12, 2004; vol. 98, pp. 397-403.

First Office Action issued in corresponding Chinese Patent Application No. 201180066956.6, issued Apr. 3, 2015. (13 pages).

Second Office Action issued in corresponding Chinese Patent Application No. 201180066956.6, dated Nov. 18, 2015, with English translation (27 pages).

* cited by examiner

SYSTEM WITH 3D USER INTERFACE INTEGRATION

FIELD OF THE INVENTION

This invention generally relates to a method and a system comprising a handheld device and at least one display.

BACKGROUND OF THE INVENTION 3D visualization is important in many fields of industry and medicine, where 3D information is becoming more and more predominant.

Displaying and inspecting 3D information is inherently difficult. To fully understand a 3D object or entire environment on a screen, the user should generally be able to rotate the object or scene, such that many or preferentially all surfaces are displayed. This is true even for 3D displays, e.g. stereoscopic or holographic, where from a given viewing position and with a given viewing angle, the user will only see some surfaces of an arbitrary 3D environment. Often, the user will also want to zoom into details or zoom out for an overview.

Various user interaction devices are in use for software that displays 3D data; these devices are: 3D mice, space balls, and touch screens. The operation of these current interaction devices requires physically touching them.

Physically touching a user-interaction device can be a disadvantage in medical applications due to risks of cross-contamination between patients or between patient and operator, or in industrial applications in dirty environments.

Several non-touch user interfaces for 3D data viewing in medical applications have been described in the literature. Vogt et al (2004) describe a touchless interactive system for in-situ visualization of 3D medical imaging data. The user interface is based on tracking of reflective markers, where a camera is mounted on the physician's head. Graetzel et al (2004) describe a touchless system that interprets hand gestures as mouse actions. It is based on stereo vision and intended for use in minimally invasive surgery.

It remains a problem to improve systems that require user interfaces for view control, which for example can be used for clinical purposes.

SUMMARY

Disclosed is a system comprising a handheld device and at least one display, where the handheld device is adapted for performing at least one action in a physical 3D environment, where the at least one display is adapted for visually representing the physical 3D environment, and where the handheld device is adapted for remotely controlling the view with which said 3D environment is represented on the display.

The system may be adapted for switching between performing the at least one action in the physical 3D environment, and remotely controlling the view with which the 3D environment is represented on the display.

The system disclosed here performs the integration of 3D user interface functionality with any other handheld device with other operating functionality, such that the operator ideally only touches this latter device that is intended to be touched. A particular example of such a handheld device is one that records some 3D geometry, for example a handheld 3D scanner.

The handheld device is a multi-purpose device, such as a dual-purpose or two-purpose device, i.e. a device both for performing actions in the physical 3D environment, such as measuring and manipulating, and for remotely controlling the view of the 3D environment on the display.

Geometrically, a view is determined by the virtual observer's/camera's position and orientation relative to the 3D environment or its visual representation. If the display is two-dimensional, the view is also determined by the type of projection. A view may also be determined by a magnification factor.

The virtual observer's and the 3D environment's position and orientation are always relative to each other. In terms of user experience in software systems with 3D input devices, the user may feel that for example, he/she is moving the 3D environment while remaining stationary himself/herself, but there is always an equivalent movement of the virtual observer/camera that gives the same results on the display. Often, descriptions of 3D software systems use the expression "pan" to indicate an apparent translational movement of the 3D environment, "rotate" to indicate a rotational movement of the 3D environment, and "zoom" to indicate a change in magnification factor.

Graphically, a view can represent a 3D environment by means of photographs or as some kind of virtual representation such as a computer graphic, or similar. A computer graphic can be rendered for example with texture and/or shading and/or virtual light sources and/or light models for surface properties. A computer graphic can also be a simplified representation of the 3D environment, for example a mesh, an outline, or an otherwise simplified representation. All or parts of the 3D environment can also be rendered with some degree of transparency. A view may represent the 3D environment in total or only parts thereof.

All of the touch-less prior art systems are 3D user interface devices only. In many prior art applications, the operator using such user interface device will also hold and work with another device that really is the central device in the overall application, e.g. a medical instrument.

It is thus an advantage of the present system that the 3D user-interface functionality is integrated in the central device, which is used for performing some kind of action.

In some embodiments the handheld device is adapted for remotely controlling the magnification with which the 3D environment is represented on the display.

In some embodiments the handheld device is adapted for changing the rendering of the 3D environment on the display.

In some embodiments the view is defined as viewing angle and/or viewing position.

In some embodiments the at least one action comprises one or more of the actions of:
  measuring,
  recording,
  scanning,
  manipulating,
  modifying.

In some embodiments the 3D environment comprises one or more 3D objects.

In some embodiments the handheld device is adapted to be held in one hand by an operator.

In some embodiments the display is adapted to represent the 3D environment from multiple views.

In some embodiments the display is adapted to represent the 3D environment from different viewing angles and/or viewing positions.

In some embodiments the view of the 3D environment in the at least one display is at least partly determined by the motion of the operator's hand holding said device.

In some embodiments the magnification represented in the at least one display is at least partly determined by the motion of the operator's hand holding said device.

In some embodiments the handheld device is adapted to record the 3D geometry of the 3D environment.

Thus the handheld device may be an intraoral dental scanner, which records the 3D geometry of a patient's teeth. The operator may move the scanner along the teeth of the patient for capturing the 3D geometry of the relevant teeth, e.g. all teeth. The scanner may comprise motion sensors for taking the movement of the scanner into account while creating the 3D model of the scanned teeth.

The 3D model of the teeth may be shown on a display, and the display may for example be a PC screen and/or the like.

The user interface functionality may comprise incorporating motion sensors in the scanner to provide that the user can determine the view on the screen by moving the scanner. Pointing the scanner down can provide that the scanned teeth are shown given a downward viewing angle. Holding the scanner in a horizontal position can provide that the viewing angle is likewise horizontal.

In some embodiments the handheld device comprises at least one user-interface element. A user-interface element is an element which the user may manipulate in order to activate a function on the user interface of the software. Typically the use interface is graphically presented on the display of the system.

The handheld device may furthermore be provided with an actuator, which switches the handheld device between performing the at least one action and remotely controlling the view. By providing such a manual switching function that enables the operator to switch between performing the at least one action and remotely controlling the view, the operator may easily control what is performed.

Such an actuator can for example be in the form of a button, switch or contact. In other embodiments it could be a touch sensitive surface or element.

In another embodiment the actuator could be a motion sensor provided in the handheld device that function as the actuator when it registers a specific type of movement, for example if the operator shakes the handheld device. Examples of such motion sensors will be described herein with respect to the user-interface element, however, the person skilled in the art will based on the disclosure herein understand that such motion sensors may also be used as actuators as discussed.

For example, the handheld device can in one embodiment be an intra-oral 3D scanner used by a dentist. The scanner is set to be performing the action of scanning a dental area when the actuator is in one position. When the actuator is switched into a second position the handheld is set to control the view with which the 3D environment is represented on the display. This could for example be that when the dentist have scanned a part of or the complete desired area of an dental arch he can activate the actuator which then allows the dentist to remotely control the view of the 3D representation of the scanned area on the display by using the handheld device.

For example, the actuator could be a button. When the button is pressed quickly the handheld device is prepared for scanning, i.e. it is set for performing at least one action, the scanning procedure, in the physical 3D environment. The scanning is stopped when the button is pressed quickly a second time.

While the scanning is performed a virtual 3D representation is visually built on the display.

The user can now press and hold the button. This will put the handheld in a controller mode, where the handheld device is adapted for remotely controlling the view with which the 3D environment, such as scanned teeth, is represented on the display. While holding the button pressed the system will use signals from a motion sensor in the handheld device to determine how to present the view of the virtual 3D environment. Thus, if the user turns or otherwise moves the hand that holds the handheld device the view of the virtual 3D environment on the display will change accordingly.

Thus, the dentist may use the same handheld device for both scanning an area and subsequently verifying that the scan has been executed correctly without having to move away from the patient or touching any other equipment than already present in his hands.

In one embodiment the user-interface element is the same as the actuator, or where several user-interface elements are present at least one also functions as an actuator.

The system may be equipped with a button as an additional element providing the user-interface functionality.

In an example the handheld device is a handheld intraoral scanner, and the display is a computer screen. The operator or user may be a dentist, an assistant and/or the like. The operation functionality of the device may be to record some intraoral 3D geometry, and the user interface functionality may be to rotate, pan, and zoom the scanned data on the computer screen.

In some embodiments the at least one user-interface element is at least one motion sensor.

Thus the integration of the user interface functionality in the device may be provided by motion sensors, which can be accelerometers inside the scanner, whose readings determine the orientation of the display on the screen of the 3D model of the teeth acquired by the scanner. Additional functionality, e.g. to start/stop scanning, may be provided by a button. The button may be located where the operator's or user's index finger can reach it conveniently.

Prior art intraoral scanners use a touch screen, a trackball, or a mouse to determine the view in the display. These prior art user interface devices can be inconvenient, awkward and difficult to use, and they can be labor-intensive, and thus costly to sterilize or disinfect. An intraoral scanner should always be disinfected between scanning different patients, because the scanner is in and may come in contact with the mouth or other parts of the patient being scanned.

The operator or user, e.g. dentist, may use one hand or both hands to hold the intraoral scanner while scanning, and the scanner may be light enough and comfortable to be held with just one hand for a longer time while scanning.

The device can also be held with one or two hands, while using the device as remote control for e.g. changing the view in the display. It is an advantage of the touchless user interface functionality that in clinical situations, the operator can maintain both hands clean, disinfected, or even sterile.

An advantage of the system is that it allows an iterative process of working in a 3D environment without releasing the handheld device during said process. For the above intraoral scanning system example, the operator, e.g. dentist, can record some teeth surface geometry with a handheld device that is an intraoral scanner, inspect coverage of the surface recording by using that same handheld device to move, e.g. rotate, the recorded surface on the display, e.g. a computer screen, detect possible gaps or holes in the coverage of the scanned teeth, and then for example arrange the scanner in the region where the gaps were located and continue recording teeth surface geometry there. Over this entire iterative cycle, which can be repeated more than once, such as as many times as required for obtaining a desired scan coverage of the teeth, the dentist does not have to lay the handheld intraoral scanner out of his or her hands.

In some embodiments, the 3D user interface functionality is exploited in a separate location than the operation functionality. For the above intraoral scanning system example, the scanning operation is performed in the oral cavity of the patient, while the user interface functionality is more flexibly exploited when the scanner is outside the patient's mouth. The key characteristic and advantage of the system, again, is that the dentist can exploit the dual and integrated functionality, that is operation and user interface, of the scanner without laying it out of his or her hands.

The above intraoral scanning system is an example of an embodiment. Other examples for operation functionality or performing actions could be drilling, welding, grinding, cutting, soldering, photographing, filming, measuring, executing some surgical procedure etc.

The display of the system can be a 2D computer screen, a 3D display that projects stereoscopic image pairs, a volumetric display creating a 3D effect, such as a swept-volume display, a static volume display, a parallax barrier display, a holographic display etc. Even with a 3D display, the operator has only one viewing position and viewing angle relative to the 3D environment at a time. The operator can move his/her head to assume another viewing position and/or viewing angle physically, but generally, it may be more convenient to use the handheld device with its built-in user interface functionality, e.g. the remote controlling, to change the viewing position and/or viewing angle represented in the display.

In some embodiments the system comprises multiple displays, or one or more displays that are divided into regions. For example, several sub-windows on a PC screen can represent different views of the 3D environment. The handheld device can be used to change the view in all of them, or only some of them.

In some embodiments the user interface functionality comprises the use of gestures.

Gestures made by e.g. the operator can be used to change, shift or toggle between sub-windows, and the user-interface functionality can be limited to an active sub-window or one of several displays.

In some embodiments the gestures are adapted to be detected by the at least one motion sensor. Gestures can alternatively and/or additionally be detected by range sensors or other sensors that record body motion.

The operator does not have to constantly watch the at least one display of the system. In many applications, the operator will shift between viewing and possible manipulating the display and performing another operation with the handheld device. Thus it is an advantage that the operator does not have to touch other user interface devices. However, in some cases it may not be possible for the operator to fully avoid touching other devices, and in these cases it is an advantage that fewer touches are required compared to a system where a handheld device does not provide any user interface functionality at all.

In some embodiments the at least one display is arranged separate from the handheld device.

In some embodiments the at least one display is defined as a first display, and where the system further comprises a second display.

In some embodiments the second display is arranged on the handheld device.

In some embodiments the second display is arranged on the handheld device in a position such that the display is adapted to be viewed by the operator, while the operator is operating the handheld device.

In some embodiments the second display indicates where the handheld device is positioned relative to the 3D environment.

In some embodiments the first display and/or the second display provides instructions for the operator.

The display(s) can be arranged in multiple ways. For example, they can be mounted on a wall, placed on some sort of stand or a cart, placed on a rack or desk, or other.

In some embodiments at least one display is mounted on the device itself. It can be advantageous to have a display on the device itself because with such an arrangement, the operator's eyes need not focus alternatingly between different distances. In some cases, the operating functionality may require a close look at the device and the vicinity of the 3D environment it operates in, and this may be at a distance at most as far away as the operator's hand. Especially in crowded environments such as dentist's clinics, surgical operation theatres, or industrial workplaces, it may be difficult to place an external display closely to the device.

In some embodiments visual information is provided to the operator on one or more means other than the first display.

In some embodiments audible information to the operator is provided to the operator.

Thus in some embodiments, the system provides additional information to the operator. In some embodiments, the system includes other visual clues shown on means other than the display(s), such as LEDs on the device. In some embodiments, the system provides audible information to the operator, for example by different sounds and/or by speech.

Said information provided to the operator can comprise instructions for use, warnings, and the like.

The information can aid with improving the action performance or operation functionality of the device, for example by indicating how well an action or operation is being performed, and/or instructions to the operator aimed at improving the ease of the action or operation and/or the quality of the action or operation's results. For example, a LED can change in color and/or flashing frequency. In a scanner, the information can relate to how well the scanned 3D environment is in focus and/or to scan quality and/or to scan coverage. The information can comprise instructions on how best to position the scanner such as to attain good scan quality and/or scan coverage. The instructions can be used for planning and/or performing bracket placement. The instructions can be in the form of a messenger system to the operator.

In some embodiments, some 3D user interface functionality is provided by at least one motion sensor built into the device. Examples of motion sensors are accelerometers, gyros, and magnetometers and/or the like. These sensors can sense rotations, lateral motion, and/or combinations thereof. Other motion sensors use infrared sensing. For example, at least one infrared sensor can be mounted on the device and at least one infrared emitter can be mounted in the surroundings of the device. Conversely, the at least one emitter can be mounted on the device, and the at least one sensors in the surroundings. Yet another possibility is to use infrared reflector(s) on the device and both sensor(s) and emitter(s) on the surroundings, or again conversely. Thus motion can be sensed by a variety of principles.

Through proper signal processing, some sensors can recognize additional operator actions; for example gestures such as taps, waving, or shaking of the handheld device. Thus, these gestures can also be exploited in the 3D user interface functionality.

In some embodiments the handheld device comprises at least two motion sensors providing sensor fusion. Sensor fusion can be used to achieve a better motion signal from for example raw gyro, accelerometer, and/or magnetometer data. Sensor fusion can be implemented in ICs such as the InvenSense MPU 3000.

In some embodiments the handheld device comprises at least one user-interface element other than the at least one motion sensor.

In some embodiments the at least one other user-interface element is a touch-sensitive element.

In some embodiments the at least one other user-interface element is a button.

In some embodiments the at least one other user-interface element is a scroll-wheel.

In some embodiments, user interface functionality is provided through additional elements on the device. Thus these additional elements can for example be buttons, scroll wheels, touch-sensitive fields, proximity sensors and/or the like.

The additional user interface elements can be exploited or utilized in a workflow suitable for the field of application of the device. The workflow may be implemented in some user software application that may also control the display and thus the view represented thereon. A given interface element can supply multiple user inputs to the software. For example, a button can provide both a single click and a double click. For example, a double click can mean to advance to a subsequent step in a workflow. For the example of intraoral scanning, three steps within the workflow can be to scan the lower mouth, the upper mouth, and the bite. A touch-sensitive field can provide strokes in multiple directions each with a different effect, etc. Providing multiple user inputs from a user interface elements is advantageous because the number of user interface elements on the device can be reduced relative to a situation where each user interface element only provides one user input.

The motion sensors can also be exploited in a workflow. For example, lifting the device, which can be sensed by an accelerometer, can represent some type of user input, for example to start some action. In a device that is a scanner, it may start scanning. Conversely, placing the device back in some sort of holder, which can be sensed by an accelerometer as no acceleration occur over some period of time, can stop said action.

If the action performed by the device is some kind of recording, for example scanning, for example 3D scanning, the results of the recording can also be exploited as user inputs, possibly along with user inputs from other user interface elements. For example, with a 3D scanner with a limited depth of field, it may be possible to detect whether any objects within the 3D environments are present in the volume corresponding to this depth of field by detecting whether any 3D points are recorded. User inputs can depend on such detected presence. For example, a button click on an intraoral scanner can provide a different user input depending on whether the scanner is in the mouth, where teeth are detectable, or significantly away from and outside the mouth. Also the effect of motion sensor signals can be interpreted differently for either situation. For example, the scanner may only change the view represented on the display when it is outside the mouth.

In some embodiments the handheld device is adapted to change a viewing angle with which the 3D environment is represented on the at least one display.

In some embodiments the handheld device is adapted to change a magnification factor with which the 3D environment is represented on the at least one display.

In some embodiments the handheld device is adapted to change a viewing position with which the 3D environment is represented on the at least one display.

In some embodiments the view of the 3D environment comprises a viewing angle, a magnification factor, and/or a viewing position.

In some embodiments the view of the 3D environment comprises rendering of texture and/or shading.

In some embodiments the at least one display is divided into multiple regions, each showing the 3D environment with a different view.

Thus in some embodiments the user interface functionality comprises changing the view with which the 3D environment is displayed. Changes in view can comprise changes in viewing angle, viewing position, magnification and/or the like. A change in viewing angle can naturally be effected by rotating the device. Rotation is naturally sensed by the aid of gyros and/or relative to gravity sensed by an accelerometer. Zooming, i.e. a change in magnification, can for example be achieved by pushing the handheld device forward and backward, respectively. A translational change of the viewing position, i.e., panning, can for example be achieved by pushing the handheld device up/down and/or sideways.

In some embodiments the user interface functionality comprises selecting or choosing items on a display or any other functionality provided by graphical user interfaces in computers known in the art. The operator may perform the selection. The Lava C.O.S scanner marketed by 3M ESPE has additional buttons on the handheld device, but it is not possible to manipulate the view by these. Their only purpose is to allow navigation through a menu system, and to start/stop scanning.

In some embodiments the user interface functionality comprises manipulating the 3D environment displayed on the screen. For example, the operator may effect deformations or change the position or orientation of objects in the 3D environment. Thus, in some embodiments the user interface functionality comprises virtual user interface functionality, which can be that the 3D data are manipulated, but the physical 3D environment in which the device operates may not be manipulated.

In some embodiments the handheld device is an intraoral scanner and/or an in-the-ear scanner. If the scanner comprises a tip, this tip may be exchanged whereby the scanner can become suitable for scanning in the mouth or in the ear. Since the ear is a smaller cavity than the mouth, the tip for fitting into an ear may be smaller than a tip for fitting in the mouth.

In some embodiments the handheld device is a surgical instrument. In some embodiments, the surgical instrument comprises at least one motion sensor, which is built-in in the instrument.

In some embodiments the handheld device is a mechanical tool. In some embodiments, the tool has at least one motion sensor built in. In other embodiments, other user-interface elements are built in as well, for example buttons, scroll wheels, touch-sensitive fields, or proximity sensors.

In some embodiment the 3D geometry of the 3D environment is known a-priori or a 3D representation of the environment is known a priori, i.e. before the actions (s) are performed. For example in surgery, a CT scan may have been taken before the surgical procedure. The handheld device in this example could be a surgical instrument that a physician needs to apply in the proper 3D position. To make sure this proper position is reached, it could be beneficial to view the 3D environment from multiple perspectives interactively, i.e. without having to release the surgical instrument.

An advantage of the system, also in the above surgery example, is the ability of the handheld device to record the 3D environment at least partially, typically in a 3D field-of-view that is smaller than the volume represented in the a-priori data. The 3D data recorded by the handheld device can be registered in real time with the a-priori data, such that the position and orientation of the device can be detected.

In some embodiments the 3D geometry comprises a 3D surface of the environment.

In some embodiments the 3D geometry comprises a 3D volumetric representation of the environment.

Thus the 3D environment can be displayed as volumetric data, or as surface, or a combination thereof. Volumetric data are typically represented by voxels. Voxels can comprise multiple scalar values. Surface data are typically represented as meshed, such as triangulated meshes, or point clouds.

The scanning may be performed by means of LED scanning, laser light scanning, white light scanning, X-ray scanning, and/or CT scanning.

The present invention relates to different aspects including the system described above and in the following, and corresponding systems, methods, devices, uses, and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a method of interaction between a handheld device and at least one display, where the method comprises the steps of:
performing at least one action in a physical 3D environment by means of the handheld device;
visually representing the physical 3D environment by the at least one display; and
remotely controlling the view of the represented 3D environment on the display by means of the handheld device.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

According to another aspect, disclosed is a system comprising a handheld device for operating in a 3D environment and at least one display for visualizing said environment, where the display is adapted to represent said environment from multiple perspectives,
where said device is adapted to be held in one hand by an operator, and where the perspective represented in the at least one display is at least partly determined by the motion of the operator's hand holding said device.

According to another aspect, disclosed is a system comprising a handheld device for operating in a 3D environment and at least one display for visualizing said environment, where the display is adapted to represent said environment in multiple views,
where said device is adapted to be held in one hand by an operator, where the view represented in the at least one display is at least partly determined by the motion of the operator's hand holding said device, and where the device has at least one touch-sensitive user interface element.

The motion of the operator's hand is typically determined by a motion sensor arranged in the handheld device.

DEFINITIONS 3D geometry: A constellation of matter or its virtual representation in a three-dimensional space.

3D environment: A constellation of physical objects each having a 3D geometry in a three-dimensional space.

View: The way a 3D environment is represented on a display. Geometrically, a view is determined by the virtual observer's/camera's position and orientation. If the display is two-dimensional, the view is also determined by the type of projection. A view may also be determined by a magnification factor. Graphically, a view can show the 3D environment by means of photographs or as some kind of virtual representation such as a computer graphic, or similar. A computer graphic can be rendered for example with texture and/or shading and/or virtual light sources and/or light models for surface properties. A computer graphic can also be a simplified representation of the 3D environment, for example a mesh, an outline, or an otherwise simplified representation. All or parts of the 3D environment can also be rendered with some degree of transparency. A view may represent the 3D environment in total or only parts thereof.

Functionality: A Purpose or Intended Use.

Performing action(s) or operating functionality: Actions or functionality that includes some type of interaction with a 3D environment, such as measuring, modifying, manipulating, recording, touching, sensing, scanning, moving, transforming, cutting, welding, chemically treating, cleaning, etc. The term "operating" is thus not directed to surgical procedures, but operating may comprise surgical procedures.

User Interface Functionality: Functionality for interaction between a human user and a machine with a display.

Handheld device: An object that has at least one functionality and that is held by a human operator's hand or both hands while performing this at least one functionality.

3D scanner: A device that analyzes a real-world object or 3D environment to collect data on its shape and possibly its appearance.

Coverage of scan: The degree to which a physical surface is represented by recorded data after a scanning operation.

Motion sensor: A sensor detecting motion. Motion can be detected by: sound (acoustic sensors), opacity (optical and infrared sensors and video image processors), geomagnetism (magnetic sensors, magnetometers), reflection of transmitted energy (infrared laser radar, ultrasonic sensors, and microwave radar sensors), electromagnetic induction (inductive-loop detectors), and vibration (triboelectric, seismic, and inertia-switch sensors). MEMS accelerometers, gyros, and magnetometers are examples of motions sensors.

Workflow: a sequence of tasks implemented in software.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
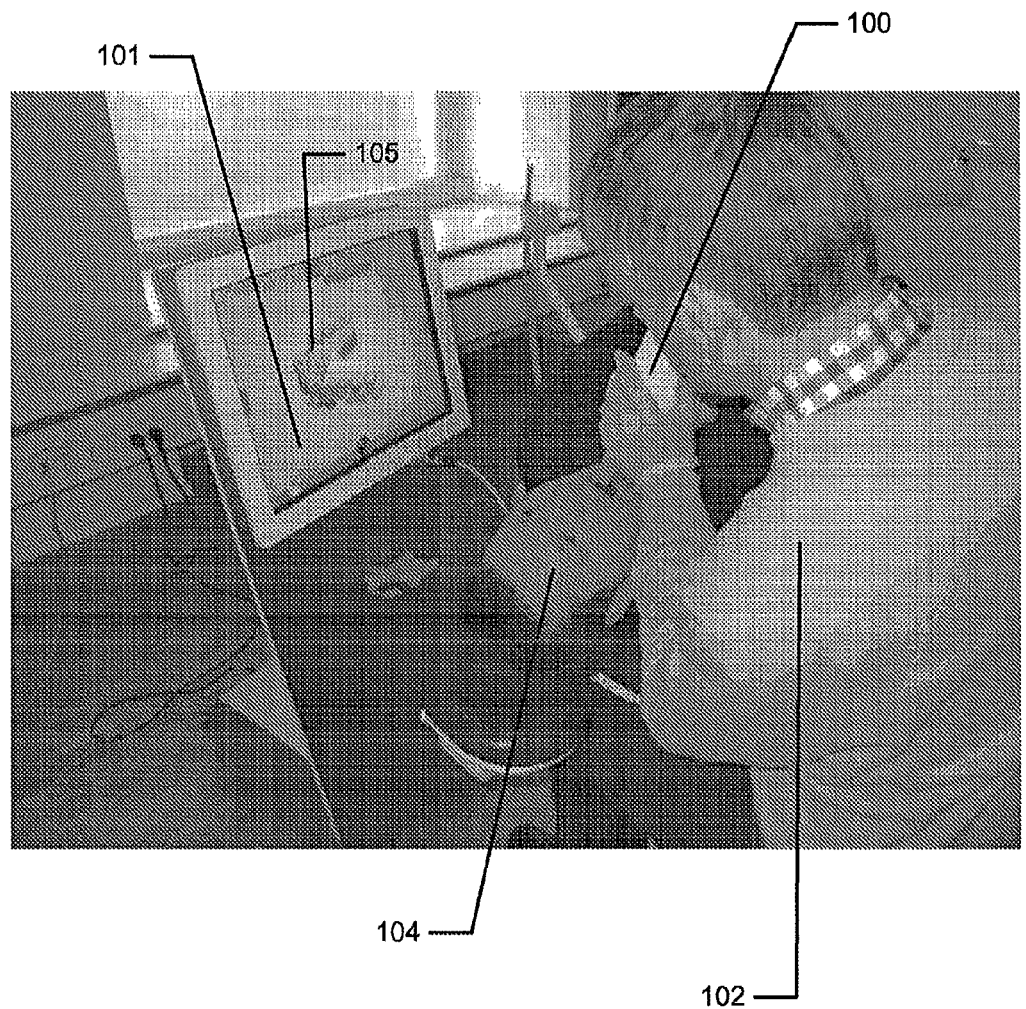
FIG. 1 shows an example of the system comprising a handheld device and a display.

FIG. 1 shows an example of the system comprising a handheld device and a display. The handheld device 100 is in this example an intraoral dental scanner, which records the 3D geometry of the patient's teeth. The operator 102 moves the scanner along the teeth of the patient 104 for capturing the 3D geometry of the relevant teeth, e.g. all teeth. The scanner comprises motion sensors (not visible) for taken the movement of the scanner into account while creating the 3D model 105 of the scanned teeth. The display 101 is in this example a PC screen displaying the data recorded by the scanner.

FIG. 2 shows an example of user interface functionality in the form of remote controlling using the handheld device. The motion sensors (not shown) in the handheld device 100, e.g. scanner, provide that the user 102 can determine the view shown on the display 101, e.g. screen, by moving the handheld device 100.

Figure 2A:
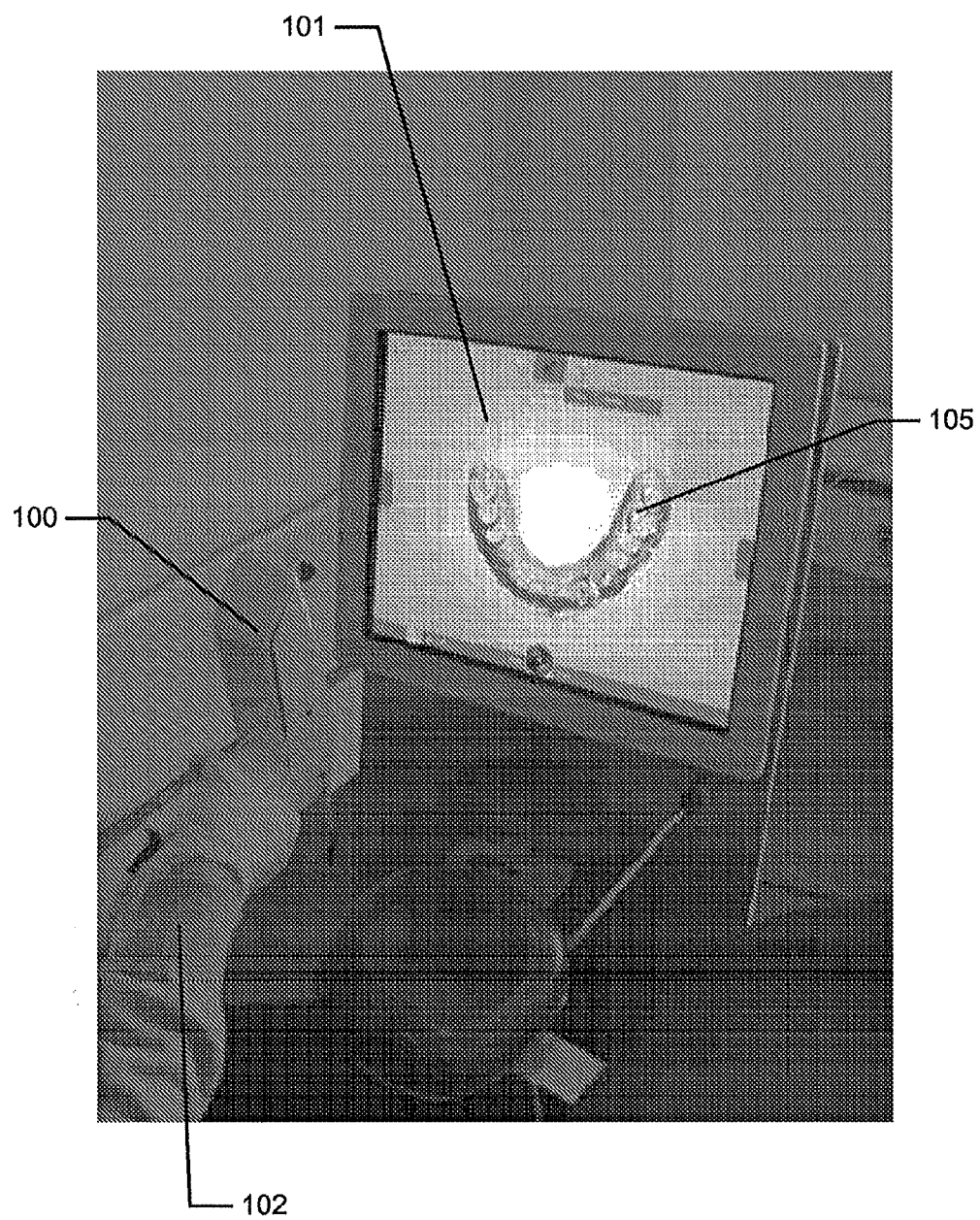
FIG. 2 shows an example of user interface functionality in the form of remote controlling using the handheld device.

FIG. 2a) shows that pointing the device 100 down can provide that the 3D model 105 of the scanned teeth is shown from a downward viewing angle.

Figure 2B:
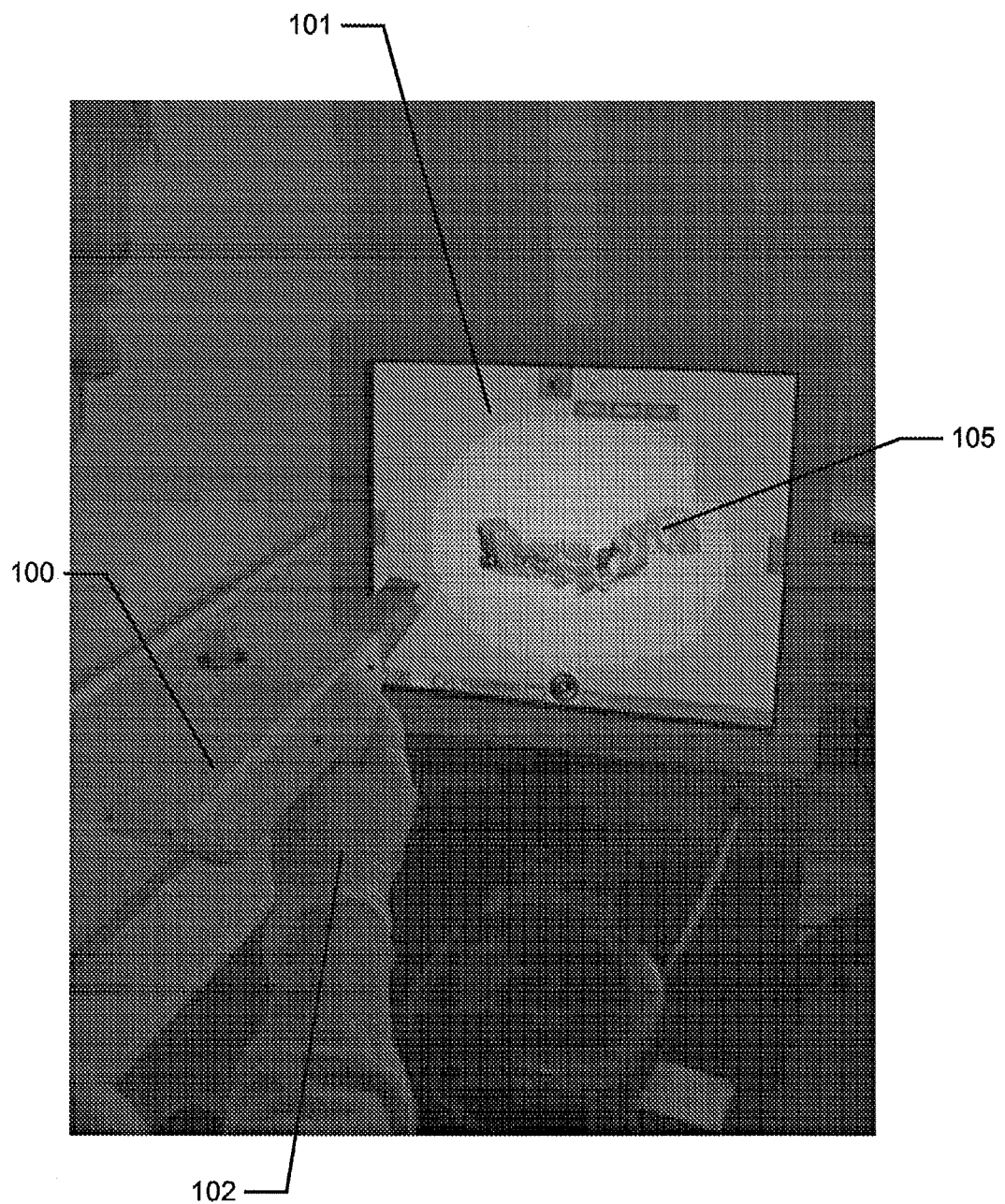

FIG. 2b) shows that holding the scanner in a horizontal position can provide that the viewing angle is likewise horizontally from the front, such that the 3D model 105 of the scanned teeth is shown from the front.

Figure 3:
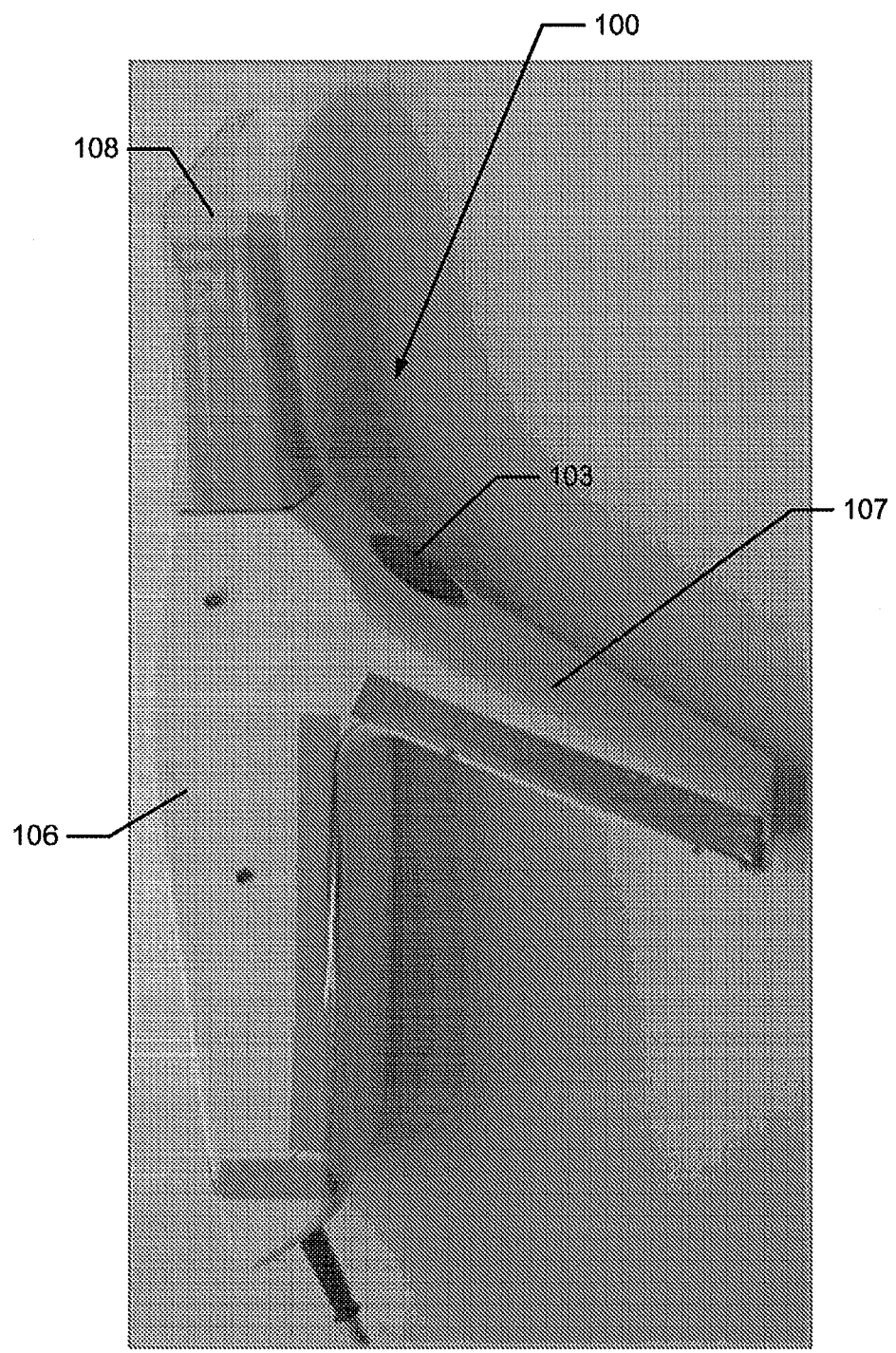
FIG. 3 shows an example of the handheld device.

FIG. 3 shows an example of the handheld device.

The handheld device 100 is in this example an intraoral scanner with a pistol-grip. The scanner comprises a housing 106 comprising the pistol-grip part 107, and a tip 108 adapted for insertion in the mouth of the patient. In this example the scanner also is equipped with a button 103 which is an additional element providing user-interface functionality.

The example system as shown in FIG. 1, FIG. 2 and FIG. 3 comprises a device 100 which is a handheld intraoral scanner and a display 101 which is a computer screen. The operator 102 may be a dentist, an assistant and/or the like. In an example, the action performance or operation functionality of the device 100 is to record some intraoral 3D geometry, and the user interface functionality is to rotate, pan, and zoom the 3D model 105 of the scanned data on the computer screen 101. The integration of the user interface functionality in the device 100 is provided by motion sensors (not visible), which can be accelerometers inside the scanner 100, whose readings determine the orientation, as seen in FIGS. 2a and 2b, of the display on the screen of the 3D model 105 of the teeth acquired by the scanner 100. Additional functionality, e.g. to start/stop scanning, may be provided by the button 103 as seen in FIG. 3. In the example system, the button 103 is located where the user's index finger can reach it conveniently.

In FIG. 1 the dentist 102 uses two hands to hold the intraoral scanner 100 while scanning, but it is understood that the scanner 100 can also be held with one hand while scanning. The device 100 can also be held with one or two hands, while changing the perspective of the 3D model 105 in the display 101. The example shown in FIG. 1 thus illustrates the advantage of the touchless user interface functionality, because in many clinical situations, the operator 102 should maintain both hands clean, disinfected, or even sterile.

The 3D user interface functionality may be exploited in a separate location than the operation functionality. For the above intraoral scanning system example, the scanning operation is performed in the oral cavity of the patient, see FIG. 1, while the user interface functionality is more flexibly exploited when the scanner is outside the patient's mouth, see FIGS. 2 and 3.

Figure 4:
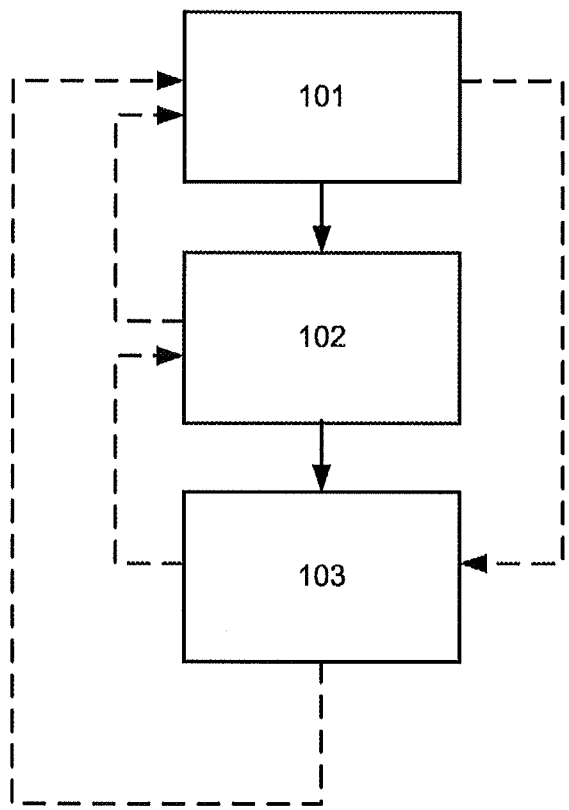
FIG. 4 shows an example of a flow-chart of a method of interaction between a handheld device and a display.

FIG. 4 shows an example of a flow-chart of a method of interaction between a handheld device and a display.

In step 101 at least one action in a physical 3D environment is performed by means of the handheld device. This action may the scanning of teeth as shown in FIG. 1.

In step 102 the physical 3D environment is visually represented by the at least one display. This may be the display of the 3D model of the scanned teeth as seen in FIG. 1.

In step 103 the view of the represented 3D environment shown on the display is remotely controlled on the display by means of the handheld device. This may be the control of the viewing angle of the 3D model as seen in FIG. 2.

All the steps of the method may be repeated one or more times. The order in which the steps are performed may be different than the order described above, which is indicated by the dotted lines in the figure. If one or more of the steps are performed more times, the order of the steps may also be different.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

LITERATURE

C. Graetzel, T. Fong, S. Grange, and C. Baur. A Non-Contact Mouse for Surgeon-Computer Interaction. Technology and Health Care, 12(3), 2004.

Vogt S., Khamene A., Niemann H., Sauer F., An AR system with intuitive user interface for manipulation and visualization of 3D medical data, Stud. Health Technol. Inform. 2004; 98, pp. 397-403.

EMBODIMENTS

The following embodiments relates to one aspect of the system as disclosed by the description herein.

1. A system comprising a handheld device and at least one display, where the handheld device is adapted for performing at least one action in a physical 3D environment, where the at least one display is adapted for visually representing the physical 3D environment, and where the handheld device is adapted for remotely controlling the view with which the 3D environment is represented on the display.

2. The system according to any one or more of the preceding embodiments, wherein the view is defined as viewing angle and/or viewing position.

3. The system according to any one or more of the preceding embodiments, wherein the handheld device is adapted for remotely controlling the magnification with which the 3D environment is represented on the display.

4. The system according to any one or more of the preceding embodiments, wherein the handheld device is adapted for changing the rendering of the 3D environment on the display.

5. The system according to any one or more of the preceding embodiments, wherein the at least one action comprises one or more of:
  measuring,
  recording,
  scanning,
  manipulating, and/or
  modifying.

6. The system according to any one or more of the preceding embodiments, wherein the 3D environment comprises one or more 3D objects.

7. The system according to any one or more of the preceding embodiments, wherein the handheld device is adapted to be held in one hand by an operator.

8. The system according to any one or more of the preceding embodiments, wherein the display is adapted to represent the 3D environment from multiple views.

9. The system according to any one or more of the preceding embodiments, wherein the view of the 3D environment represented in the at least one display is at least partly determined by the motion of the operator's hand holding said device.

10. The system according to any one or more of the preceding embodiments, wherein the magnification represented in the at least one display is at least partly determined by the motion of the operator's hand holding said device.

11. The system according to any one or more of the preceding embodiments, wherein the handheld device is adapted to record the 3D geometry of the 3D environment.

12. The system according to any one or more of the preceding embodiments, wherein the 3D geometry of the 3D environment is known a-priori.

13. The system according to any one or more of the preceding embodiments, wherein the handheld device comprises at least one user-interface element.

14. The system according to any one or more of the preceding embodiments, wherein the at least one user-interface element is at least one motion sensor.

15. The system according to any one or more of the preceding embodiments, wherein the handheld device comprises at least two motion sensors providing sensor fusion.

16. The system according to any one or more of the preceding embodiments, wherein the user interface functionality comprises the use of gestures.

17. The system according to any one or more of the preceding embodiments, wherein the gestures are detected by the at least one motion sensor.

18. The system according to any one or more of the preceding embodiments, wherein the handheld device comprises at least one user-interface element other than the at least one motion sensor.

19. The system according to any one or more of the preceding embodiments, wherein the at least one other user-interface element is a touch-sensitive element.

20. The system according to any one or more of the preceding embodiments, wherein the at least one other user-interface element is a button.

21. The system according to any one or more of the preceding embodiments, wherein the at least one other user-interface element is a scroll wheel.

22. The system according to any one or more of the preceding embodiments, wherein the handheld device is adapted to change a viewing angle with which the 3D environment is represented on the at least one display.

23. The system according to any of the preceding embodiments, wherein the handheld device is adapted to change a magnification factor with which the 3D environment is represented on the at least one display.

24. The system according to any one or more of the preceding embodiments, wherein the handheld device is adapted to change a viewing position with which the 3D environment is represented on the at least one display.

25. The system according to any one or more of the preceding embodiments, wherein the view of the 3D environment comprises a viewing angle, a magnification factor, and/or a viewing position.

26. The system according to any one or more of the preceding embodiments, wherein the view of the 3D environment comprises rendering of texture and/or shading.

27. The system according to any one or more of the preceding embodiments, wherein the at least one display is divided into multiple regions, each showing the 3D environment with a different view.

28. The system according to any one or more of the preceding embodiments, wherein the 3D geometry comprises a 3D surface of the environment.

29. The system according to any one or more of the preceding embodiments, wherein the 3D geometry comprises a 3D volumetric representation of the environment.

30. The system according to any one or more of the preceding embodiments, wherein the handheld device is an intra-oral 3D scanner.

31. The system according to any one or more of the preceding embodiments, wherein the handheld device is a surgical instrument.

32. The system according to any one or more of the preceding embodiments, wherein the handheld device is a mechanical tool.

33. The system according to any one or more of the preceding embodiments, wherein the handheld device is an in-ear 3D scanner.

34. The system according to any one or more of the preceding embodiments, wherein the at least one display is arranged separate from the handheld device.

35. The system according to any one or more of the preceding embodiments, wherein the at least one display is arranged on a cart.

36. The system according to any one or more of the preceding embodiments, wherein the at least one display is defined as a first display, and where the system further comprises a second display.

37. The system according to any one or more of the preceding embodiments, wherein the second display is arranged on the handheld device.

38. The system according to any one or more of the preceding embodiments, wherein the second display is arranged on the handheld device in a position such that the display is adapted to be viewed by the operator, while the operator is operating the handheld device.

39. The system according to any one or more of the preceding embodiments, wherein the second display indicates where the handheld device is positioned relative to the 3D environment.

40. The system according to any one or more of the preceding embodiments, wherein the first display and/or the second display provides instructions for the operator.

41. The system according to any one or more of the preceding embodiments, wherein visual information is provided to the operator on one or more means other than the first display.

42. The system according to any one or more of the preceding embodiments, wherein audible information to the operator is provided to the operator.

43. The system according to any one or more of the preceding embodiments, wherein the scanning is performed by means of LED scanning, laser light scanning, white light scanning, X-ray scanning, and/or CT scanning.

44. A method of interaction between a handheld device and at least one display, where the method comprises the steps of:
performing at least one action in a physical 3D environment by means of the handheld device;
visually representing the physical 3D environment by the at least one display; and
remotely controlling the view of the represented 3D environment on the display by means of the handheld device.

45. A computer program product comprising program code means for causing a data processing system to perform the method of any one or more of the preceding embodiments, when said program code means are executed on the data processing system.

46. A computer program product according to the previous embodiment, comprising a computer-readable medium having stored there on the program code means.

The invention claimed is:

1. A scanning system for scanning a 3D environment, the scanning system comprising:
a handheld device including an optical scanner, wherein the 3D environment to be scanned is selected by pointing the optical scanner at the 3D environment; and
at least one display remotely connected to the handheld device,
wherein the handheld device is adapted for performing at least one scanning action in a physical 3D environment, and the at least one display is adapted for visually representing the physical 3D environment; and
the handheld device includes a user interface for remotely controlling the display to adjust the view with which the 3D environment is represented on the display.

2. A system according to claim 1, wherein the handheld device is adapted to record the 3D geometry of the 3D environment.

3. A system according to claim 1, wherein the user interface includes means for manually switching between performing the at least one scanning action and remotely controlling the view.

4. The system according to claim 1, wherein the handheld device comprises at least one motion sensor.

5. The system according to claim 4, wherein the view of the 3D environment represented in the at least one display is at least partly determined by the at least one motion sensor.

6. The system according to claim 4, wherein functionality of the user interface comprises a use of gestures.

7. The system according to claim 6, wherein the gestures are detected by the at least one motion sensor.

8. The system according to claim 4, wherein the user-interface is other than the at least one motion sensor.

9. The system according to claim 1, wherein the handheld device is adapted to change a viewing angle with which the 3D environment is represented on the at least one display.

10. The system according to claim 1, wherein the handheld device is adapted to change a magnification factor with which the 3D environment is represented on the at least one display.

11. The system according to claim 1, wherein the handheld device is an intra-oral 3D scanner.

12. The system according to claim 1, wherein the handheld device includes a surgical instrument.

13. The system according to claim 1, wherein the handheld device includes a mechanical tool.

14. The system according to claim 1, wherein the handheld device is an in-ear 3D scanner.

15. The system according to claim 1, wherein the at least one display is defined as a first display, and where the system further comprises a second display.

16. The system according to claim 15, wherein the second display indicates where the handheld device is positioned relative to the 3D environment.

17. The system according to claim 15, wherein the first display and/or the second display provides instructions for the operator.

18. The system according to claim 1, wherein audible information is provided to the operator.

19. A system comprising:
a handheld device and at least one display;
wherein the handheld device is adapted for switching between performing at least one action in a physical 3D environment, wherein the at least one display is adapted for visually representing the physical 3D environment; and remotely controlling the display to adjust the view with which the 3D environment is represented on the display;
wherein the handheld device is an intra-oral 3D scanner and the at least one action performed in the physical 3D environment is scanning and that the view is remotely controlled by at least one motion sensor arranged in the handheld device, and wherein an actuator provided on the handheld device switches between performing the at least one action and remotely controlling the view.

* * * * *